US007700629B2

(12) United States Patent
Sudo et al.

(10) Patent No.: US 7,700,629 B2
(45) Date of Patent: *Apr. 20, 2010

(54) USE OF A NON-RACEMIC MIXTURE OF BUPIVACAINE ENANTIOMERS, FOR IMPROVING THE ANESTHESIA PROFILE

(75) Inventors: Roberto T. Sudo, Rio de Janeiro (BR); Valter F. T. Russo, Itapira (BR); Elisa M. S. Russo, Itapira (BR)

(73) Assignee: Cristalia Productos Quimicos Farmaceuticos Ltda, Sao Paulo (BR)

( * ) Notice: Subject to any disclaimer, the term of this patent is extended or adjusted under 35 U.S.C. 154(b) by 0 days.

This patent is subject to a terminal disclaimer.

(21) Appl. No.: 11/806,624

(22) Filed: Jun. 1, 2007

(65) Prior Publication Data

US 2007/0249681 A1  Oct. 25, 2007

Related U.S. Application Data

(62) Division of application No. 10/868,224, filed on Jun. 16, 2004, now abandoned, which is a division of application No. 10/240,827, filed as application No. PCT/BR01/00040 on Apr. 5, 2001, now abandoned.

(30) Foreign Application Priority Data

Apr. 6, 2000  (BR) .................................... 0002246

(51) Int. Cl.
    *A61K 31/4458* (2006.01)
    *C07D 211/32* (2006.01)
(52) U.S. Cl. ...................... 514/330; 514/331; 546/229
(58) Field of Classification Search ................ 514/330, 514/331; 546/229
    See application file for complete search history.

(56) References Cited

U.S. PATENT DOCUMENTS 4,302,465 A   11/1981   Ekenstam et al.

(Continued)

FOREIGN PATENT DOCUMENTS

WO    WO-95/10276    4/1995

(Continued)

OTHER PUBLICATIONS

Caplus Enlish Abstract Tobert JA, Clin. Pharmacol. Ther. vol. 29 (1981).*

*Primary Examiner*—Rita J Desai
(74) *Attorney, Agent, or Firm*—Birch, Stewart, Kolasch & Birch, LLP

(57) ABSTRACT

The present invention describes a new method for the separation of bupivacaine enantiomers consisting in a continuous separation process performed without heating, by the selective precipitation of their diastereomeric salts with tartaric acid. This heatless process avoids the degradation of the reagents granting a continuous process feature to the procedure.

Another embodiment of the present invention is related to the enantiomeric manipulation of bupivacaine enantiomers in order to obtain pharmaceutical compositions presenting several enantiomeric excess of levobupivacaine to quantify and determinate the role of the dextrobupivacaine on its anesthetic and cardiotoxic effects. These enantiomeric manipulated compositions showed to present an expressive improvement on its anesthetic properties that had shown to be similar to racemic bupivacaine presenting a cardiotoxic profile similar to enantiomeric pure levobupivacaine.

3 Claims, 6 Drawing Sheets

Sensorial Block

U.S. PATENT DOCUMENTS

| | | |
|---|---|---|
| 5,708,011 A | 1/1998 | Bardsley et al. |
| 5,849,763 A | 12/1998 | Bardsley et al. |
| 5,994,548 A | 11/1999 | Langston et al. |

FOREIGN PATENT DOCUMENTS

| | | |
|---|---|---|
| WO | WO-96/09290 A1 | 3/1996 |
| WO | WO-96/12699 A1 | 5/1996 |
| WO | WO-96/22281 A1 | 7/1996 |
| WO | WO-02/067896 | 9/2002 |

* cited by examiner

FIGURE 1: Structure of bupivacaine's enantiomers
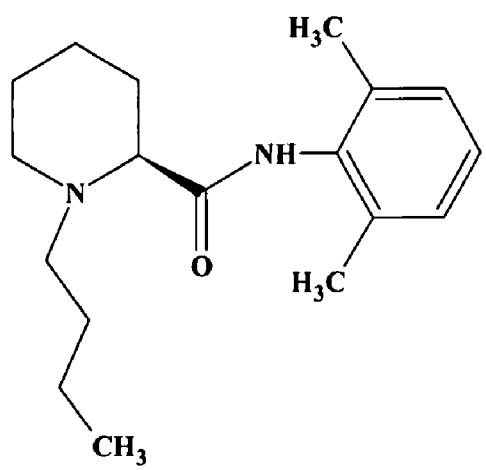
LEVOBUPIVACAINE
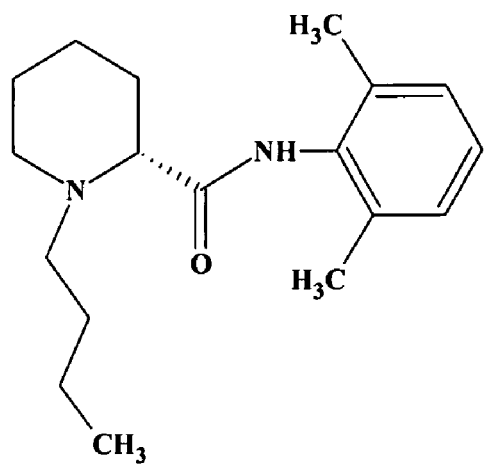
DEXTROBUPIVACAINE

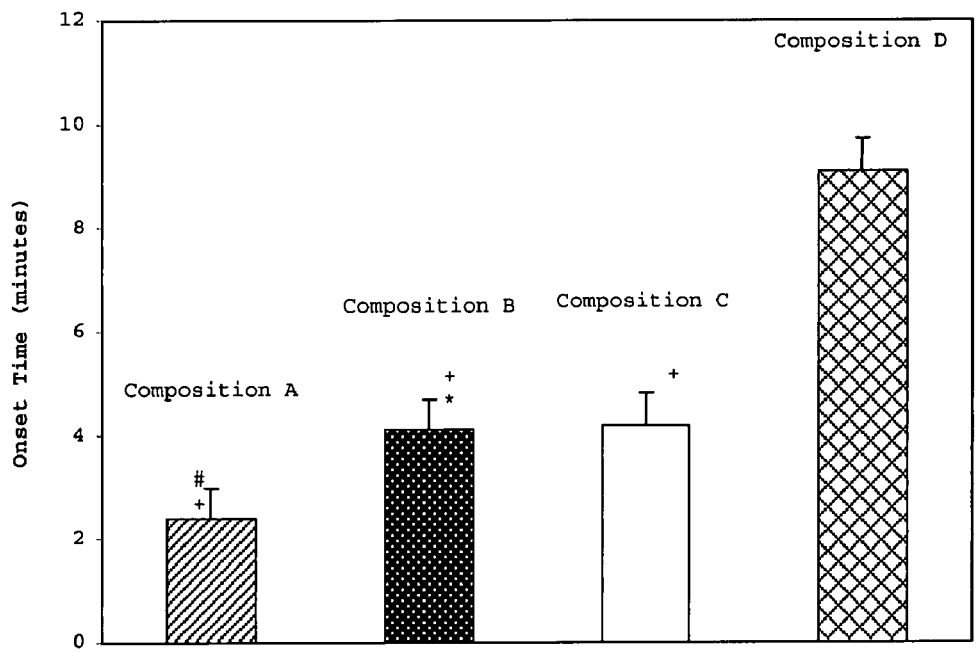
FIGURE 2: Onset time
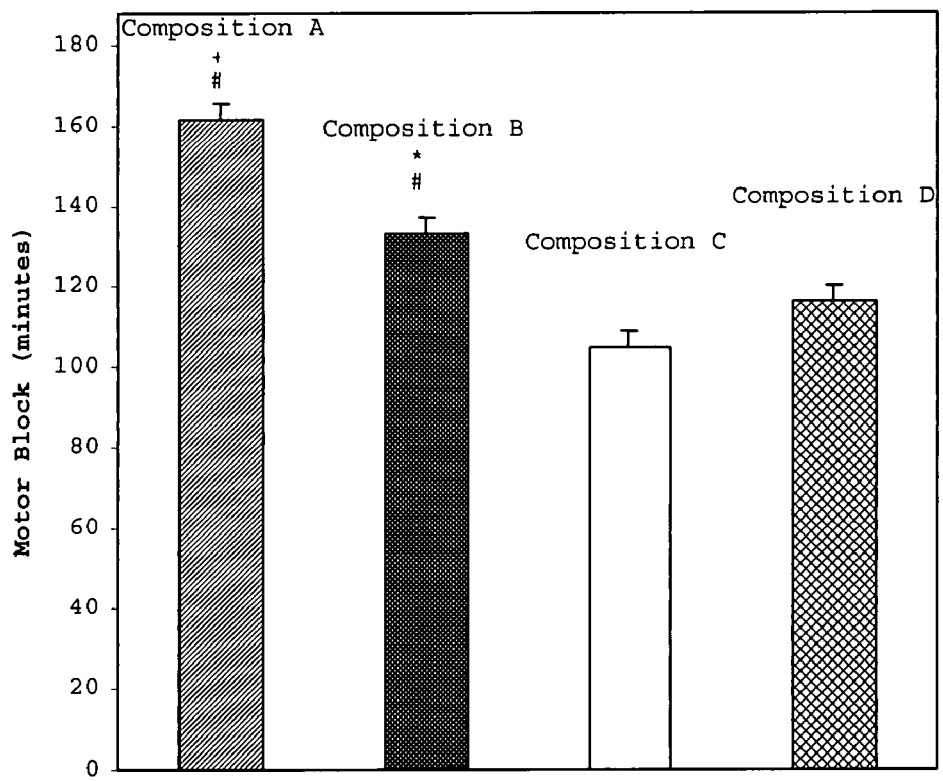
FIGURE 3: Motor Block Duration

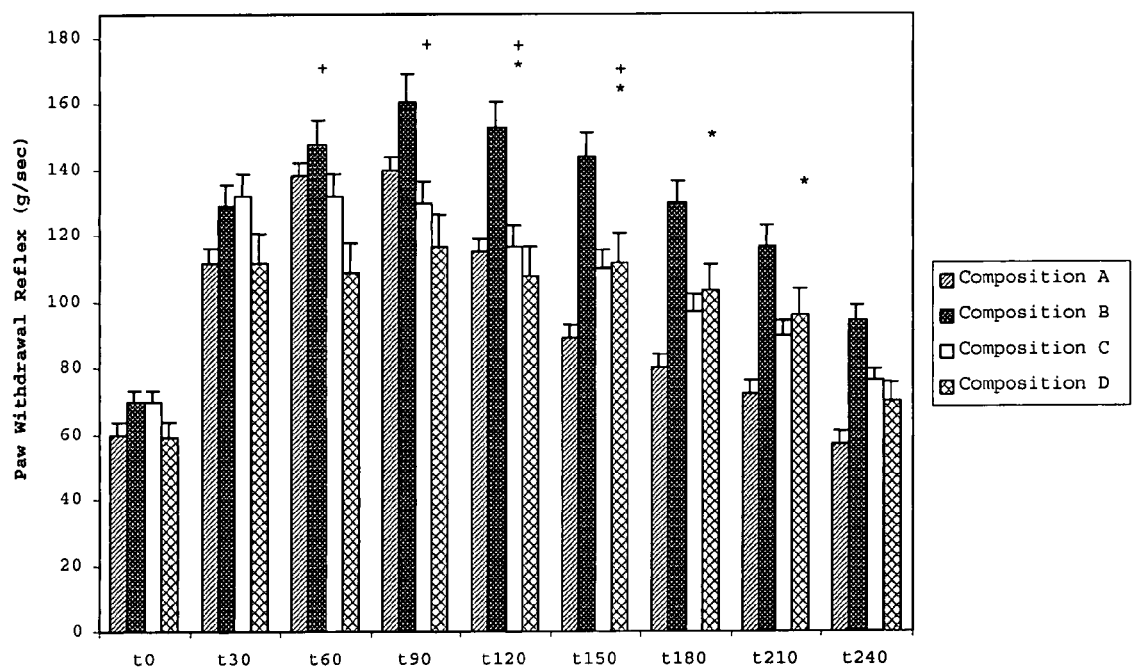
FIGURE 4: Sensorial Block

FIGURE 5 - L.A. EFFECT OVER M.A.P.
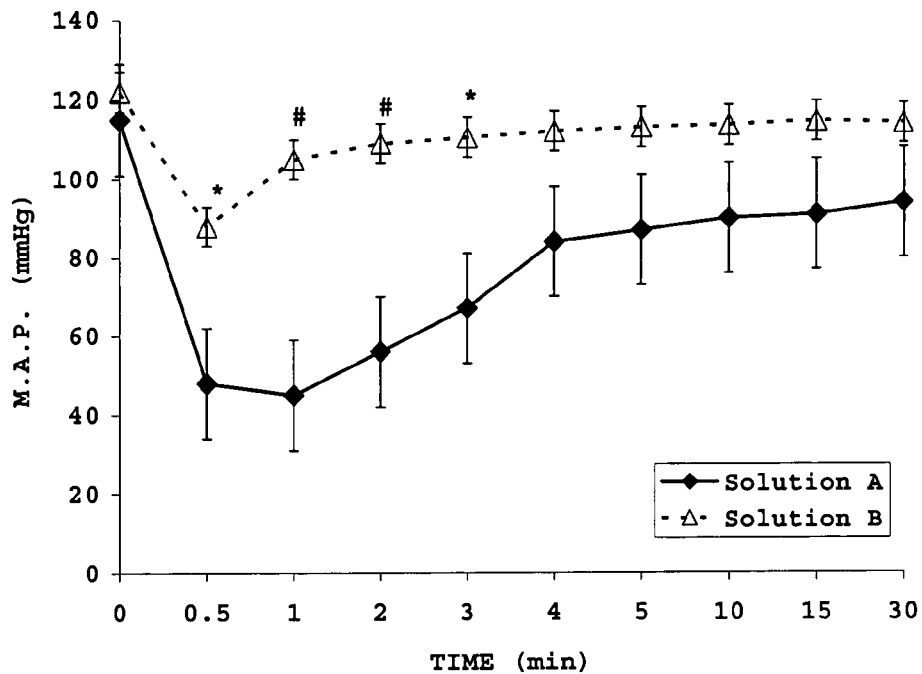
FIGURE 6 - L.A. EFFECT OVER M.A.P.
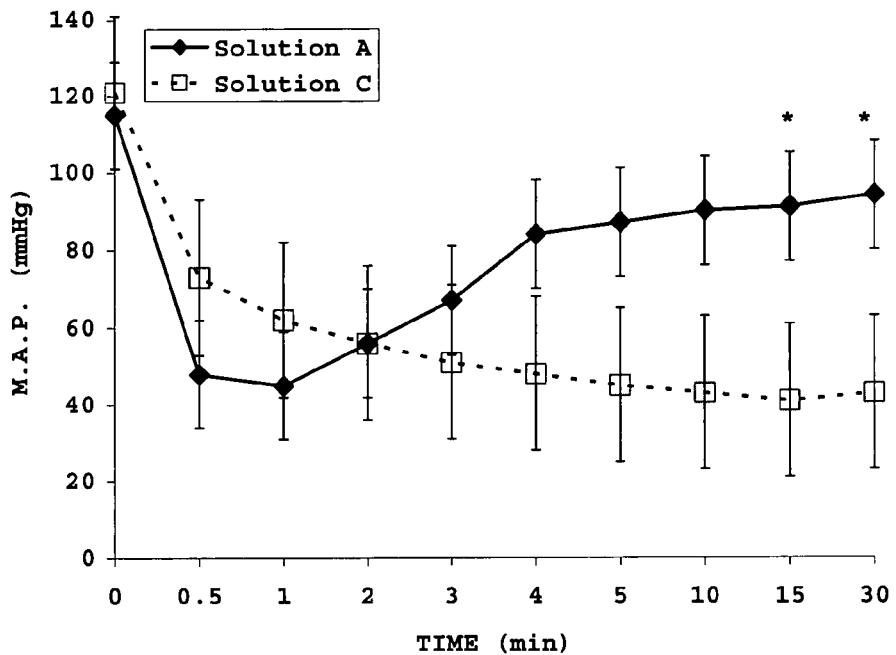

FIGURE 7 - L.A. EFFECT OVER M.A.P.
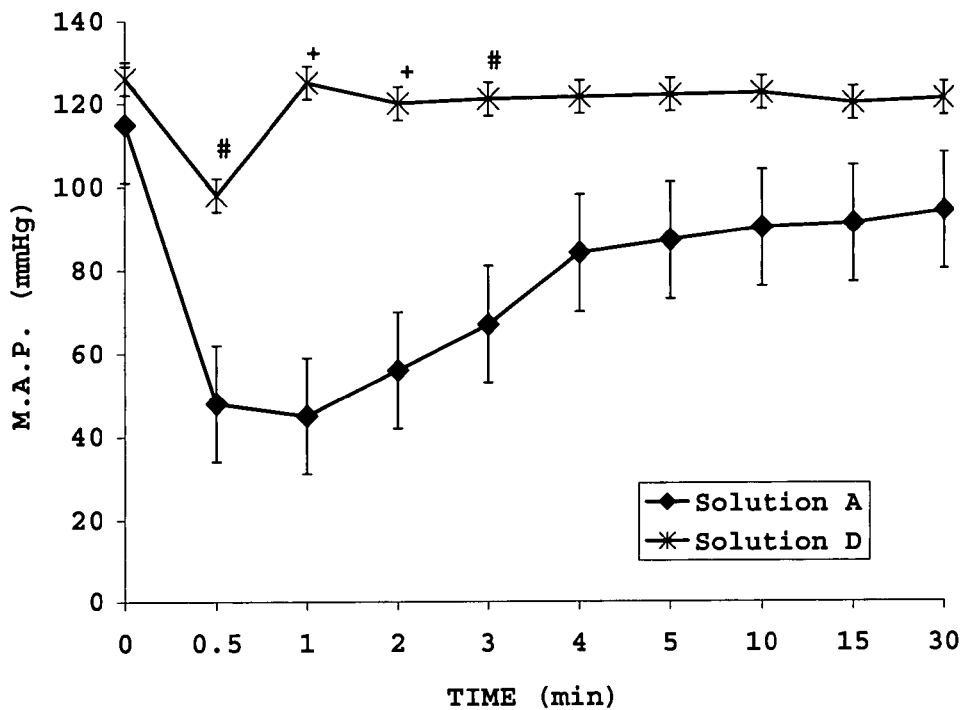
FIGURE 8 - L.A. EFFECT OVER M.A.P.
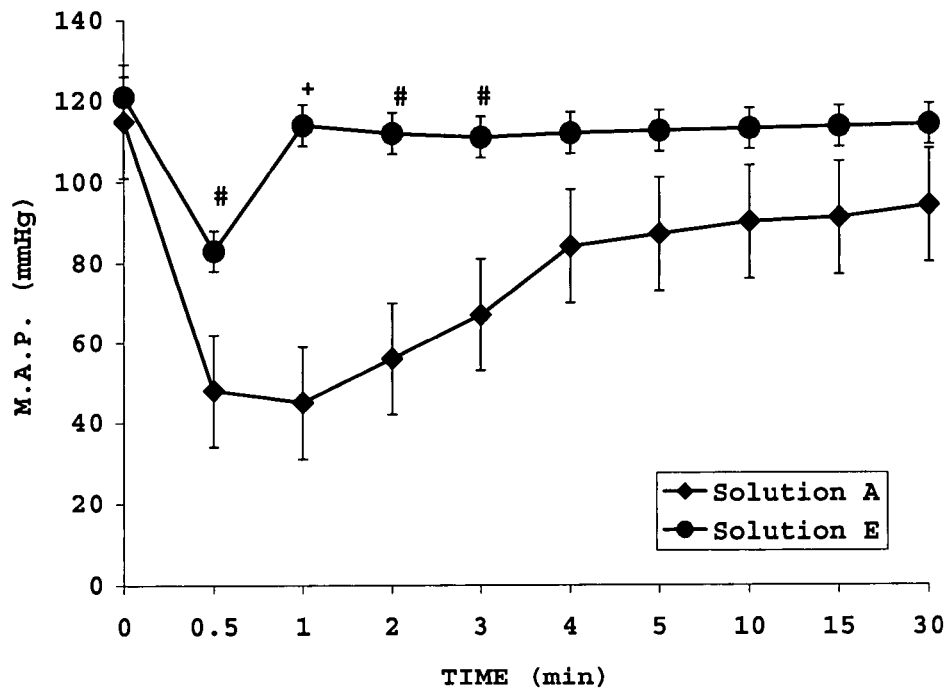

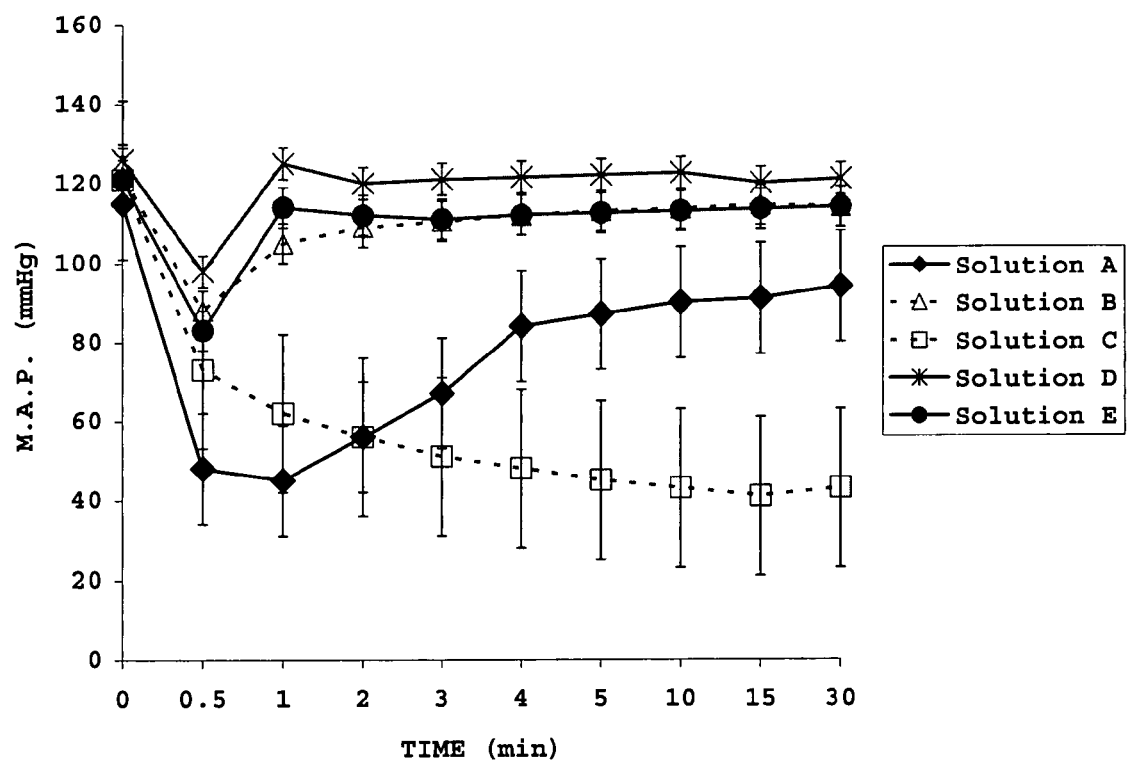

USE OF A NON-RACEMIC MIXTURE OF BUPIVACAINE ENANTIOMERS, FOR IMPROVING THE ANESTHESIA PROFILE

This application is a Divisional of application Ser. No. 10/868,224, filed on Jun. 16, 2004 now abandoned, which is a Divisional of application Ser. No. 10/240,827, now abandoned, and for which priority is claimed under 35 U.S.C. § 120. application Ser. No. 10/240,827 is the U.S. National phase application of PCT/BR01/00040, filed on Apr. 5, 2001 now abandoned and for which priority is also claimed. This application also claims priority to Application No. PI0002246-2 filed in Brazil on Apr. 6, 2000, under 35 U.S.C. § 119. The entire contents of all applications are hereby incorporated by reference The present invention is basic related with pharmacological field, more precisely with the anesthesiology field.

Enantiomeric concept is related to molecules that when presenting one or more asymmetric carbons, said chiral carbons, these molecules are not superimposable upon their mirror images. The different optic isomers are denominated enantiomers. The enantiomers of the same substance on their pure forms present the property of rotating the plane-polarized light in a certain number of degrees. The enantiomer that rotates the plane-polarized light to the right is called dextroisomer and it is able of doing that in the same numbers of degrees that the enantiomer that rotates the plane-polarized light to the left, so called levoisomer.

Racemic mixtures are mixtures of equal quantities of both enantiomers. These mixtures are optically inactive (as they do not present specific rotation) because rotations of opposite sides cancel each other.

The separation process of the enantiomers from a racemic mixture is denominated resolution.

Chemical reactions when give rise to chiral molecules originate racemic compounds, except in cases related to asymmetric synthesis. Most of the active pharmaceutical ingredients that present chiral molecules are nowadays used as racemic mixtures.

By the evolution of 3D-Biochemistry, mainly in the stereoisomeric field, advances had come into view that made possible a better understanding of the interaction between enantiomer-receptor once those enantiomers are able to produce different pharmacological effects, although having similar physical-chemical properties.

These different pharmacological effects are due to different selectivity from the enantiomers in relation to specific receptors and/or enzymes. These enantiomers are metabolized in different rates and with different affinities from tissues and docking sites of proteins. This is due to the spatial arrangement of the chiral carbon, where atoms or atoms groups are linked in different positions in space, forming 3D-relationships with an ambient not less asymmetric from the receptors or enzymes made from chiral amino acids, the L-amino acids (Simonetti M P B, Batista, R A, Ferreira, F M C—Esterioisomeria: a interface da tecnologia industrial de medicamentos e da racionalização terapêutica. Rev. Bras. Anestesiol., 48(5): 390-399 (1998)).

When an enantiomer exhibits a high degree of affinity for the activity site (eutomer) it may interferes in the action of its antipode, inactivating it (distomer). To this phenomenon Ariens EJ called isomeric ballast (Stereochemistry, a basis for sophisticated nonsense in pharmacokinetics and clinical pharmacology" Eur. J. Clin. Pharmacol., 26: 663-668(1994)). This is the case of atropine that is naturally produced as an S-enantiomer and during its extraction process racemizes resulting in the relationship S/R 50:50, being the R-enantiomer completely inactive as anticholinergic. In the clinic it is used as a racemic compound.

Twenty five percent of drugs nowadays in medicine use have one or more chiral carbons, being 80% marketed in their racemic form (Calvey T N—Chirality in Anesthesia, Anesthesia, 47: 93-94 (1992)).

The enantiomeric inactive form (distomer), however is not always a passive component of the mixture and can act as an agonist, antagonist, exerts actions on other receptors, produces unpleasant side effects and even contributes to the global efficacy of the racemate (Williams K, Lee E—Importance of drug enantiomers in clinical pharmacology, Drugs, 30: 333-354 (1985)).

Some examples are presented as follows on which we may find differences in the activities between the enantiomers of racemic drugs regularly commercialized: ketamine contains the S-ketamine that is predominantly anesthetic and hypnotic, and the R-ketamine is the main responsible for its undesirable side effects (psychic reactions on awakening); in the case of propoxyphene the (2S,3R)-(−)-propoxyphene is antitussive while the (2R,3S)-(+)-propoxyphene is analgesic; the prilocalne has the R-prilocalne isomer that being faster metabolized than S-prilocalne induces the increase of the plasmatic concentration of o-toluidine and methemoglobinemia.

Bupivacaine is a chiral molecule, and is used nowadays as its racemic form. It has two enantiomers: levorotatory or levobupivacaine and the dextrorotatory or dextrobupivacaine (FIG. 1).

At the beginning it was believed that bupivacaine enantiomers had the same local anesthetic potency. However, recent studies in the sciatic nerve of frog conducted by Lee-Son et al (Lee-Son M B, Wang G K, Concus A, et al—Stereoselective inhibition of neural sodium channels by local anesthetics, Anesthesiology, 77: 324-335 (1992)), demonstrated that dextrobupivacaine was more potent than levobupivacaine, inducing a tonic and phasic block with potency 2 to 3 times greater.

Recently Valenzuela et al demonstrated "in vitro" the greater stereoselectivity of dextrobupivacaine, in terms of potency and affinity by sodium and potassium channels in the hart in relation with levobupivacaine. The difference related to the initially observed toxicity by Aberg (Aberg G. Toxicological and local anaesthetic effects of optically active isomers of two local anesthetic compounds—Acta Pharmacol. Toxicol., 31: 273-286 (1972)) was confirmed by the experiments conducted by Gristwood et al in volunteers comparing levobupivacaine with racemic bupivacaine, allowing to conclude that dextrobupivacaine acts by contributing with the toxic effects of this local anesthetic (Valenzuela C, Snyders D J, Bennet P B—Stereoselective block of cardiac sodium channels by bupivacaine in guinea pig ventricular myocytes. Circulation, 92(10): 3014-24 (1995); Valenzuela C, Delpon E, Tamkun M M—Stereoselective block of a human cardiac potassium channel by bupivacaine enantiomers, Biophys. J., 69: 418-427 (1995); Gristwood R, Bardley H, Baker H, et al—Reduced cardiotoxicity of levobupivacaine compared with racemic bupivacaine (Marcaine): New clinical evidence. Exper. Opin. Ivest. Drugs, 3: 1209-1212 (1994)).

With the recent advances of synthetic techniques and in the separation of enantiomers, the pharmaceutical industry is making possible the obtainment of pure enantiomers, allowing a significant increase of therapeutic indices of drugs until this moment used as racemates.

The obtainment of bupivacaine enantiomers on their pure forms, allowed a better understanding about the mechanism of action of bupivacaine and revealed the contribution of dextrobupivacaine on the cardiotoxic potential of this anesthetic.

Clinical trials conducted in Brazil also demonstrated that the reduction of the cardiotoxicity attained by pure levobupivacaine was followed by the reduction of its clinical potency, which can lead to unsatisfactory results as mentioned by Mathias R S (Mathias R S—Levobupi—Uma nova opção de anestésico local com menor toxicidade, 44° Congresso Brasileiro de Anesthesiologia 1997—Belohorizonte—MG). With effect, pure levobupivacaine had demonstrated unsatisfactory results considering the quality of neural block in large surgical procedures, requiring a complementation of the anesthetic technique, as it was observed with ropivacaine, another anesthetic recently introduced in the market.

Otherwise evidenced by Mathias in Brazil, world references show much more reticence in relation to the anesthetic profile of levobupivacaine. There is an agreement about the cardiotoxic profile of this enantiomer that actually presents lower cardiotoxicity when compared to racemic bupivacaine. There are some uncertain results that seam to show a lower anesthetic potential related to this enantiomer. Among them there are the results obtained by Dyhre et al (Dihre H, L$_o$ang M, Wallin R & Renck H—The duration of action of bupivacaine, levobupivacaine, ropivacaine and pethidine in peripheral nerve block in the rat—Acta Anaesthesiol. Scand., 41(10): 1346-1352 (1997)) from Lyons et al (Lyons G, Columb M, Wilson R C & Lohnson R V—Epidural pain relief in labor: potencies of levobupivacaine and racemic bupivacaine—Br. J. Anaesth., 81(6): 899-910 (1998)) and in the Patent WO 99/04771 reporting that the duration of motor block with levobupivacaine is relatively inferior when compared with racemic bupivacaine.

Although the majority of international studies about the efficiency of neural blocks obtained with levobupivacaine appear to be vague, it seams to have a growing tendency on promoting the utilization of higher concentrations of this new drug (equal or superior than 0.75%), probably trying to compensate the inferior activity of levobupivacaine. This tendency may be observed in several patents and in the studies of some researchers like Cox et al and Kopacz et al (Cox C R, Faccenda K A, Gilhooly C, Scott N B, Bannister J & Morrinson L M—Extradural S-(−)-bupivacaine: Comparison with recemic RS-bupivacaine—Br. J. Anaesth. 80(3): 289-293 (1998); Kopacz D J, Allen H W & Thompson G E—Double-blind randomized trial of 0.75% levobupivacaine compares to 0.75% bupivacaine for epidural anesthesia in patients undergoing major elective abdominal surgery—Anesth. Analg., 86, 2S (1998)).

However, increasing in concentrations of the compositions prepared with levobupivacaine should conduct directly to the increase of their cardiotoxicity, with the consequent disappearing of the initial clinic advantage of a minor cardiotoxicity inherent to levobupivacaine.

Among the related published patents there are the patents numbers WO 95/10276 and WO 95/10227 identified in Brazil as PI 1100590 and PI 1100586 respectively. These patents disclose about lower cardiotoxicity of levobupivacaine in relation with dextrobupivacaine and racemic bupivacaine. Their authors claim the use of levobupivacaine with an enantiomeric excess preferably higher than 90%, more preferably higher than 99%. The concentrations of the pharmaceutical compositions prepared with this active pharmaceutical ingredient are from 0.25% (m/v) to 0.75% (m/v).

Patent number WO 96/32109 identified in Brazil as PI 9604891, also discloses about the cardiotoxicity of racemic bupivacaine and the lesser cardiotoxicity of its levoisomer. As in the previous patents the enantiomeric excess are preferably at least 90%, more preferably at least of 99% in levobupivacaine. This patent is directed to its use in pregnant women anesthesia, being the concentrations of those compositions higher than the concentrations used for racemic bupivacaine. These concentrations oscillate from a minimum of 0.75% (m/v) and may be increased to concentrations of 2.0% (m/v) of levobupivacaine.

Patent number WO 98/38996 also discloses about the inferior cardiotoxicity of levobupivacaine in relation to its dextroisomer and racemic bupivacaine. The levoisomer is also used in an enantiomeric excess of at least 90%, more preferably at least 99%. The concentrations of the pharmaceutical compositions are between 0.25% (m/v) and 1.5% (m/v).

Patent number WO 98/38997 discloses about the synergistic effect observed between opioids and $\alpha_2$-agonists in relation to levobupivacaine. Once again levobupivacaine is used in an enantiomeric excess of at least 90%, more preferably at least 99%. It discloses that the synergistic effect observed allows the decreasing in concentration of levobupivacaine in the pharmaceutical compositions.

Patent number WO 98/38999 discloses the use of levobupivacaine in an enantiomeric excess of at least 90%, more preferably at least 99%. The concentrations of the pharmaceutical compositions are from 0.25% (m/v) to 2.0% (m/v). Its application is for pediatric usage.

Patents numbers WO 99/04771 and WO 99/0472 also claim the use of levobupivacaine in an enantiomeric excess of at least 99%. The concentrations of the possible pharmaceutical compositions are from 0.75% (m/v) and 2.0% (m/v) of levobupivacaine.

From all the patents listed above it is possible to extract important features. Among them it is possible to verify that the levobupivacaine used in the studies performed until now presents high enantiomeric excess, and there is no reference about the associated effects on using lower enantiomeric excesses. It is observed the great strictness on studying levobupivacaine preferably free from its dextroenantiomer, in an enantiomeric excess of at lest 99%, and there is not any mention to the possible effects related to the presence of small definite quantities of dextrobupivacaine. There is no study about the use of levobupivacaine in enantiomeric excess lesser than 99%.

The utilization of both enantiomers to reach a desired pharmacological profile or an ideal therapeutic effect of a drug is not a novel procedure in the field, and is employed in some circumstances. Indacrinone was one of the first drugs on which the manipulation of both enantiomers demonstrated the improvement on its activity. Its levoenantiomer demonstrated to be a natriuretic agent more potent than its dextroenantiomer. The relatively high uricosuric/natriuretic rate of its dextroenantiomer, offered the opportunity to improve the pharmacological profile of this drug. The enantiomeric manipulation of indacrinone was conducted expecting to observe if the increasing in the dextroenantiomer/levoenantiomer rate could prevent or revert the hyperuricemic effect of its racemate, without inducing natriuresis. This study demonstrates that the ideal proportions between its dextroenantiomer and levoenantiomer was from 60% to 77% of an enantiomeric excess of its dextroenantiomer (Tobert J A, Cirillo V J, Hitzenberger G, James I, Pryor J, Cook T, Brentinx S, Holmes I B & Lutterbeck P M—Clin. Pharmacol. Ther. 29: 344-350 (1981)).

The second important feature derived from these patents, is related to the tendency on using higher concentrations in pharmaceutical compositions. These concentrations are in some instances higher than the twice the maximum concentration suggested to be used for racemic bupivacaine. On the other side there is no reference in the previous literature that states that levobupivacaine is so lesser toxic as suggested by those patents in order to justify the use of so high concentrations, mainly in pediatrics, pregnancy and in cardiac compromised patients.

Racemic bupivacaine is nowadays marketed in 0.25%, 0.50% and 0.75% concentrations. Higher concentrations are not formulated because of its high toxicity. Even 0.75% concentration is not used on all procedures due the elevated risk associated to an accidental intravascular administration.

From the studies performed on the toxicity of levobupivacaine, several researchers estimate that it is around 30% to 40% lower in relation to racemic bupivacaine (Aberg G—Toxicological and local anaesthetic effects of optically active isomers of two local anaesthetic compounds—Acta Pharmacol. Toxicol., 31: 273-286 (1972); Luduena F P, Bogado E F & Tullar B F—Optical isomers of mepivacaine and bupivacaine—Arc. Int. Pharmacodyn., 200: 359-369 (1972); Vanhoutte F, Vereecke J, Verbeck N, Carmellet E—Brit. J. Pharmacol., 103: 1275-1281 (1991)). These therapeutic indices do not justify the use of so high concentrations as proposed in the above patents.

As we emphasized before, these higher concentrations of levobupivacaine in the pharmaceutical compositions are going to eliminate its better quality and the reason for its development, the inferior cardiotoxicity.

With the objective of obtainment of bupivacaine enantiomers, there are several available references in the literature. Among them it is possible to mention the procedure described in the "Journal of Medicinal Chemistry, 14(9): 891-892 (1971)" that describes a separation process for bupivacaine enantiomers by using selective precipitation of its diastereomeric salts with natural tartaric acid, from high concentrated solutions using high temperatures on dissolution of the reagents. The experimental execution of this procedure shows to be an extremely delicate process, depending on features like cooling rates, stirring conditions, batch size among others that directly interfere on the stability of the solution and in the purity of the precipitated product. Besides, most of the times the separation of the diasteriomeric salts do not occur and both tartrates precipitate together.

Patent GB 1180712 (1970) from Luduena and Tullar, describes two different processes on the separation of bupivacaine enantiomers, one of them using isopropanol as solvent and the other using acetone. Both procedures are conducted at elevated temperatures and high concentrations, being unfeasible to conduct the process in a continuous way due the decomposition of the reagents on standing for long times at high temperatures and also due to the variable purity of the tartrate salt isolated.

Patent WO 96/12699 from Mariene Langson alternatively suggests the use of D-(-)-tartaric acid, precipitating directly the salt containing the levoenantiomer by a procedure involving high temperatures. This procedure also could not be conducted in a continuous operation due its reagents decomposition and besides, the resolution agent also known as unnatural tartaric acid, is ten to twenty times more expensive than natural tartaric acid, elevating considerably its production cost.

The present invention describes a new process to separate the enantiomers from racemic bupivacaine. One of the objectives of the present invention is the process of separating the enantiomers from racemic bupivacaine. This process consists in the formation of diastereomeric salts employing a tartaric acid as resolution agent. The tartaric acid preferably used is the L-(+)-tartaric acid, however the process can be conducted with similar results by using D-(-)-tartaric acid, noticing the change in the salts used to seed the solutions and the inversion in the order of the precipitated tartrates. The solvent preferably used in this resolution is acetone, but the procedure can be performed in aqueous ethanol, methanol and isopropanol.

In this procedure the obtainment of the diastereomers is performed in a diluted solution of the organic solvent, which gives the enough stability to the reaction mixture yielding the tartrates in a constant enantiomeric purity. Their separation is performed in small portions, but in a continuous process from the mother liquors. As this process do not use heating there is neither thermal degradation nor racemization of the resolution agent and no thermal degradation of the substrate either (racemic bupivacaine), being not necessary the substitution of the mother liquors.

Due those features described above the separation process acquires a character of continuous process and can be easily automated in order to simplify its monitoring, lowering the production costs.

The resolution procedure consists in dissolving the substrate on its free base form and the L-(+)-tartaric acid at room temperature in a suitable solvent. This solution is firstly seeded with dextrobupivacaine tartrate and is kept under stirring for a few hours. Dextrobupivacaine tartrate precipitates and it is separate from the reaction mixture by filtration. The filtrate is then seeded with levobupivacaine tartrate and kept under stirring for a few hours, while precipitation of levobupivacaine tartrate occurs. This salt is separated and the reaction mixture is reconstituted to its original proportions of tartaric acid and bupivacaine, and the solvent is completed to its initial amount. Seeding with dextrobupivacaine tartrate restarts the process and the above procedure is repeated.

According to the resolution process described, the molar relationship between bupivacaine free base and the resolution agent may be from 1:0.6 to 1:1.2. The concentration of the reaction mixture may be from 0.1M to 0.4M in relation to racemic bupivacaine free base. Temperatures may be from 15° C. to 30° C. and the time necessary to the precipitation of each tatrate salt may be from 4 to 10 hours.

The respective free bases (dextrobupivacaine and levobupivacaine free bases) are obtained by the dissolution of the respective tartrates salts in water, resulting in solutions with concentrations from 0.05M to 0.4M, and the subsequent treatment with alkaline solutions (sodium hydroxide, ammonium hydroxide and other bases) in order to adjust the final pH of the solution in a range from 7 to 13. During this treatment precipitates the free base that is separated by filtration or centrifugation. Enriched dextrobupivacaine and levobupivacaine so obtained present enantiomeric excess of about 70% to 80%. The obtainment of pure enantiomers (ee>99%) may be achieved by simple recrystallization from isopropanol or another suitable solvent.

The respective hydrochloride salts may be obtained by dissolution of these bases in suitable organic solvents followed by the addition of hydrochloric acid in a concentrated aqueous solution or in gas.

Another embodiment of the present invention is based on the prior verification that the dextroenantiomer of bupivacaine seems to represent an important role in the potency and duration of the anesthetic effect that may be the complement of the expected activity of its levoenantiomer. Its absence in levobupivacaine compositions affects directly the duration and deepness of the anesthetic effects, being necessary higher dosages of this enantiomer to reach the desired levels of anesthesia and anesthetic duration effect.

We verified that there is no study performed to determinate the possible contribution of low definite quantities of the dextroenantiomer on the anesthetic effect of levobupivacaine compositions.

In addition, another objective of the present invention is to provide the enantiomeric manipulation of levobupivacaine, by lowering the enantiomeric excess of its levoisomer, quantifying the contribution of the dextroenantiomer on the anesthetic and cardiotixic effects, in order to improve the anesthetic profile of levobupivacaine.

Another embodiment of the present invention is the process of obtainment of the pharmaceutical compositions based on levobupivacaine prepared with their free base forms or their pharmaceutical acceptable salts.

The enantiomeric manipulation in order to obtain levobupivacaine with enantiomeric excess lower than 99% (ee<99%), may be achieved by several procedures known in the art. For example, but not limited to these procedures, it can be achieved from the pure enantiomers on their solid states or in solutions, or can be achieved by the mixture of racemic bupivacaine with levobupivacaine on their solid states or in solutions. In the described procedure, enriched levobupivacaine obtained directly from its tartrate salt may have its enantiomeric excess adjusted by the addition of pure levobupivacaine or dextrobupivacaine, and even racemic bupivacaine, in order to achieve the desired enantiomeric excess. The monitoring of the enantiomeric excess may be done by HPLC with chiral column to guarantee the achievement of the desired enantiomeric excess.

By these enantiomeric manipulation procedures described above, and analysis of the final enantiomeric excess by HPLC, there may be prepared several compositions between levobupivacaine and dextrobupivacaine in order to obtain the most variable enantiomeric excess on levobupivacaine.

We could notice that the addition of the dextroenantiomer in definite quantities in order to lower the enantiomeric excess on levobupivacaine confer to the compositions using this combined active ingredient, properties equivalent to those existing in levobupivacaine in respect to its lower cardiotoxicity and properties equivalent to racemic bupivacaine in respect to the efficiency on neural blocks.

BRIEF DESCRIPTION OF THE DRAWINGS

The invention may be better understood by reference to the drawings wherein:

FIG. 1 shows the structure of both levobupivacaine and dextrobupivacaine;

FIG. 2 is a graph showing onset time for various compositions;

FIG. 3 is a graph showing motor block duration for various compositions;

FIG. 4 is a graph showing sensorial block for various composition;

FIG. 5 is a graph showing local anesthetic effect over mean arterial pressure, abbreviated "L.A. effect over M.A.P." comparing solutions A and B;

FIG. 6 is a graph showing L.A. effect over M.A.P. comparing solution A and c;

FIG. 7 is a graph showing L.A. effect over M.A.P. comparing solutions A and D;

FIG. 8 is a graph showing L.A. effect over M.A.P. comparing solutions A and E; and FIG. 9 is a graph showing L.A. effect over M.A.P. comparing solution A, B, C, D and E.

The studies we are going to present demonstrate that there are ideal relationships between the bupivacaine enantiomers, being these relationships different from the existing 1:1 found in racemic bupivacaine, and different from the existing in the levobupivacaine used in the studies published until now, that were performed using this enantiomer on its almost enantiomeric pure form (ee>99%).

According to the present invention the compositions from levobupivacaine and dextrobupivacaine may have an enantiomeric excess in levobupivacaine from preferably 90% to 20%, more preferably from 80% to 30% and more preferably yet from 70% to 40%.

The resulting active ingredients, comprehended in this enantiomeric excess range, may be used in several pharmaceutical compositions on their free base forms or their pharmaceutical acceptable salts. The pharmaceutical compositions may be prepared in analogy with the existent in the market for racemic bupivacaine as well those active pharmaceutical ingredients may be employed in novel pharmaceutical compositions.

According to the surprising and significant improvement in the pharmacological profile of these pharmaceutical compositions, prepared with the active ingredients manipulated on their enantiomeric proportions, these formulated pharmaceutical compositions may be employed in the same final concentrations nowadays used for racemic bupivacaine, although conferring a lower associated cardiotoxicity than bupivacaine and equivalent to the cardiotoxicity observed on levobupivacaine, besides conferring an equivalent anesthetic effect to the observed with racemic bupivacaine.

Another objective of the present invention is the use of the pharmaceutical compositions based on levobupivacaine formulated with their free bases or their pharmaceutical acceptable salts.

The experiments described forward are illustrative but are not limited on demonstrating the obtainment of bupivacaine enantiomers as well they exemplify the proportions between the enantiomers in order to obtain compositions with different enantiomeric excess in levobupivacaine, illustrating the described technique. In addition, it is presented two studies performed using the pharmaceutical compositions prepared with active ingredients enantiomeric manipulated, studies that demonstrate the improvement on the pharmacological profile of those compositions, retaining its lower cardiotoxicity property inherent to levobupivacaine.

The following examples are illustrative of the obtainment process of bupivacaine enantiomers:

EXAMPLE 1

Separation of Racemic Bupivacaine Enantiomers in a Continuous Process

A reactor fitted with mechanical stirring was charged with 10 liters of acetone, 288.4 g (1.0 mol) of bupivacaine base and 151.1 g (1.0 mol) of L-(+)-tartaric acid. The mixture was kept under stirring at ambient temperature until complete dissolution of the solids. To the resulting solution was added 1 g of dextrobupivacaine tartrate and the system was kept under stirring for approximately 7 hours. During this period the precipitation of dextrobupivacaine tartrate was complete. The solids were filtered and the filtrate was returned to the reactor. It was added 1 g of levobupivacaine tartrate and the solution was kept under stirring for approximately 7 hours for the precipitation of levobupivacaine tartrate. The solids were separated and the liquid returned to the reactor. It was charged with 57.7 g of racemic bupivacaine and 30.0 g of L-(+)-tartaric acid. Acetone was added to complete the initial volume and the procedure was restarted by the total dissolution of the solids, addition of dextrobupivacaine tartrate seeds and keeping the solution under stirring for approximately 7 hours to complete the precipitation of dextrobupivacaine tartrate, and so on.

Dextrobupivacaine tartrate—Each batch yields m≦45 g MP=178-186° C.

Levobupivacaine tartrate—Each batch yields m≦45 g MP=110-120° C.

EXAMPLE 2

Obtainment of Enriched Levobupivacaine 45 g of levobupivacaine tartrate were dissolved in 222 mL of water under stirring. Concentrated ammonium hydroxide was added under stirring until the pH adjusted at 9-10. The solids were filtered and washed with 222 mL of water. The solids were dried in an oven with temperature around 45° C. until constant weight. Yield 27.6 g of enriched levobupivacaine free base (70%≦ee≦80%), MP=125-132° C.

EXAMPLE 3

Obtainment of Enriched Dextrobupivacaine

By the same procedure described in the example 2, but using 45 g of dextrobupivacaine tartrate in the place of levobupivacaine tartrate it was obtained 27g of enriched dextrobupivacaine free base (70%≦ee≦80%), MP=125-132° C.

EXAMPLE 4

Preparation of Pure Levobupivacaine 27.6 g of enriched levobupivacaine free base obtained in the example 2 were recrystallized from 138 mL of hot isopropanol, yielding 22.3 g of pure levobupivacaine free base with ee>99.5% and MP=135-137° C. $[\alpha]^D_{25}=-80°$ (c=2, MeOH).

EXAMPLE 5

Preparation of Pure Dextrobupivacaine 27 g of enriched dextrobupivacaine free base obtained by the procedure described in example 3, were recrystallized from 135 mL of hot isopropanol, yielding 23.3 g of pure dextrobupivacaine (ee>99.5%), MP=135-137° C., $[\alpha]^D_{25}=+80°$ (c=2, MeOH).

EXAMPLE 6

Preparation of Levobupivacaine Hydrochloride 23.3 g of pure levobupivacaine free base were dissolved in 125 mL of hot isopropanol. To this solution was added 8.8 mL of concentrated hydrochloric acid. The solution was cooled to room temperature and kept at a temperature between 4° C. to 6° C. for two hours. The mixture was vacuum filtered and the solids were stirred with 20 mL of acetone. The mixture was filtered and the solid was allowed to dry in an oven yielding 24.2 g of levobupivacaine hydrochloride ee>99.5%, MP=246-250° C., $[\alpha]^D_{25}=-12$ (c=2, H$_2$O).

EXAMPLE 7

Preparation of Dextrobupivacaine Hydrochloride

Dextrobupivacaine hydrochloride may be obtained by the same procedure described in example 6, by substituting pure levobupivacaine free base by pure dextrobupivacaine free base obtained in the example 5. The obtained product presents ee>99.5%, MP=247-250° C. $[\alpha]^d_{25}=+12°$ (c=2, H$_2$O).

Studies Conducted with Active Ingredients Manipulated on Their Enantiomeric Relationships.

Study 1

To perform this study it was prepared the compositions with active ingredients containing the enantiomeric proportions described in table 1 presented below:

TABLE 1

|  | % mass levobupivacaine | % mass dextrobupivacaine | % enantiomeric excess |
|---|---|---|---|
| Composition A | 90 | 10 | 80 |
| Composition B | 75 | 25 | 50 |
| Composition C | 100 | 0 | >99.5 |
| Composition D | 50 | 50 | 0 |

This study was designed to investigate the influence from the presence of pre-determined quantities of dextrobupivacaine in formulations of levobupivacaine to determine the influence of the dextroenantiomer on the sciatic nerve of the rat "in vivo". The final concentration (% on total mass) of the formulations was 0.5%.

Method:

44 male Wistar rats were divided into 4 groups and injected in the periarticular space of the right hind limb, according to Truant's modified technique (Simonetti M P B, Valinetti E A, Ferreira F M C—Braz. Journal Anesthesiol. Int. Issue, 9:65-72 (1998)). The following variables were studied: onset, motor block duration and sensory block intensity. To evaluate the sensory block intensity the animals were submitted to a pressoric stimuli (g/sec) in an Analgesy Meter by the Randall-Selitto test. A limit of 300 g/sec was adopted to avoid tissue injury. The onset of the effect from the injection of 0.2 mL of each 0.5% solution was evaluated by hyperextension of the hind limb. Motor block was defined as the time elapsed between the onset and the disappearance of such signal. The paw withdrawal reflex (PWR) was assessed in order to study the sensory block. This parameter was evaluated in the following periods: t0 (baseline), t30, t60, t90, t120, t150, t180, t210, t240.

Results:

The results obtained in this experiment were grouped in tables 2 and 3 presented below:

TABLE 2

Onset time and duration of motor block with compositions A, B, C and D.

| Anesthetic | Onset time | Motor block duration |
|---|---|---|
| Composition A | 2.4 ± 0.2 (n = 10) | 161.5 ± 2.8 (n = 10) |
| Composition B | 4.1 ± 0.2 (n = 10) | 133.0 ± 4.7 (n = 10) |
| Composition C | 4.2 ± 0.3 (n = 12) | 104.6 ± 4.3 (n = 12) |
| Composition D | 9.1 ± 0.5 (n = 12) | 116.2 ± 3.5 (n = 12) |

TABLE 3

Sensory block evaluated by the paw withdrawal reflex (g/sec) with compositions A, B, C and D.

| Local Anesthetic | t0 | t30 | t60 | T90 | t120 | t150 | t180 | t210 | t240 |
|---|---|---|---|---|---|---|---|---|---|
| Composition A | 60 ± 2 | 112 ± 5 | 138 ± 4 | 140 ± 3 | 115 ± 4 | 89 ± 4 | 80 ± 3 | 72 ± 2 | 57 ± 2 |
| Composition B | 70 ± 3 | 129 ± 5 | 148 ± 3 | 161 ± 2 | 153 ± 3 | 144 ± 4 | 130 ± 6 | 117 ± 5 | 94 ± 2 |
| Composition C | 70 ± 3 | 132 ± 4 | 132 ± 5 | 130 ± 5 | 117 ± 5 | 110 ± 5 | 97 ± 4 | 90 ± 4 | 76 ± 6 |
| Composition D | 59 ± 3 | 112 ± 9 | 109 ± 7 | 117 ± 8 | 112 ± 6 | 108 ± 6 | 103 ± 4 | 96 ± 7 | 70 ± 7 |

Discussion: The effects of the bupivacaine enantiomers demonstrate to be stereospecific. The obtained results showed that the mixtures play an important role on the efficacy of local anesthesia, in terms of onset and duration of neural block (FIGS. 2 and 3). The FIG. 2 presents the onset time results, where "+" symbol represents the statistic significant indices $P<0.01$ in relation to Composition D, "*" symbol represents statistic significance indices $p<0.01$ in relation to composition A and the symbol "#" represents statistic significance indices $P<0.001$ in relation to composition C. FIG. 3 presents the results of duration of neural block, where "+" symbol represents significant difference in relation to composition D with $p<0.001$, the "*" symbol represents significative difference in relation to composition A with $p<0.05$ and the "#" symbol represents significative difference in relation to composition C, with $p<0.01$. Both parameters were improved in Composition A (ee=80%). These results show that dextrobupivacaine must contribute to efficacy of sodium channels nerve block. On the other hand, the action on fibers A-delta and C seems to require a relative higher concentration of dextrobupivacaine, once the greater analgesic activity was observed with the composition B (FIG. 4). The FIG. 4 presents the results of sensorial block, where "+" symbol represents statistic significance indices $p<0.05$ in relation to composition D and the "*" symbol represents the statistic significance indices $p<0.05$ in relation to composition C. The relevance of this investigation points out that there are effective differences on activity presented by pharmaceutical compositions prepared with lower enantiomeric excess of levobupivacaine studied until this moment.

Study 2

The following study had the objective to determinate the effects of different compositions prepared on the cardiovascular system, medium arterial pressure (MAP) and heart rate.

Method:

35 rats were anesthetized with sodium pentobarbital (30 mg/kg i.p.). Jugular vein and carotid artery were cannulated for injection of the local anesthetics and monitoring the medium arterial pressure; ECG was recorded. Each rat was injected with 2.0 mg/kg in bolus.

It was used solutions with a final concentration of 0.5% (in mass) of the active ingredients listed in Table 4.

The monitoring of the enantiomeric excess of the solutions was carried out by HPLC analysis.

The results of the assays over cardiovascular system, mean arterial pressure and heart rate were submitted by statistic treatment with one-way ANOVA. $p<0.05$ was considered statistically significant.

TABLE 4

Active ingredients employed in the anesthetic solutions prepared.

| Local Anesthetic | Composition |
|---|---|
| Solution A | Racemic bupivacaine |
| Solution B | Levobupivacaine (ee > 99.5%) |
| Solution C | Dextrobupivacaine (ee > 99.5%) |
| Solution D | 10% in mass of dextrobupivacaine + 90% in mass of levobupivacaine (ee 80%) |
| Solution E | 25% in mass of dextrobupivacaine + 75% in mass of levobupivacaine |

Results:

All local anesthetic solutions decreased the mean arterial pressure and the heart rate 30 seconds after their administration. After 1 minute, rats that took solutions B, D, and E, had those parameters back the basal level. Rats that took solution A, had those parameters back for the basal level only after 4 minutes. Solution C, prepared with pure dextrobupivacaine induced cardiovascular collapse and death in five from 7 rats tested.

The FIGS. 5 to 8 represents the results of the time course of local anesthetic effects over mean arterial pressure for the single experiments and FIG. 9 for all experiments. FIGS. 5 to 8 represent the time course of local anesthetic effect (L.A.Effect) over mean arterial pressure (M.A.P.), where the "*" symbol is $p<0.05$ and "#" is $p<0.01$ and "+" $p<0.001$ (data expressed by mean±standard medium error n=9/group). FIG. 9 represents the L.A.Effect over M.A.P. where data are expressed by mean±standard medium error (n=9/group).

Discussion:

Solutions D and E did not induce cardiodepressing effects. The proportions used of the dextroenantiomer in these formulations showed to be in reality less harmful than racemic bupivacaine (solution A). The effects of these compositions presenting lower enantiomeric excess on levobupivacaine seen to be similar to the effects of pure levobupivacaine over cardiovascular system, besides inducing a superior neural block.

The invention claimed is:

1. A method for sensory and motor nerve block comprising contacting the nerve with a pharmacologically effective amount of a pharmaceutical composition comprising an active ingredient consisting of levobupivacaine (l) and dextrobupivacaine (d), or pharmaceutically acceptable salts thereof, wherein the weight ratio of (l):(d) is 75:25.

2. A method of anesthetizing a subject comprising administering a pharmaceutical composition comprising an active ingredient consisting of levobupivacaine (l) and dextrobupivacaine (d) or pharmaceutically acceptable salts thereof, wherein the weight ratio of (l):(d) is 75:25, to a subject in need thereof.

3. A method for sensory and motor nerve block comprising contacting the nerve with a pharmacologically effective amount of a pharmaceutical composition comprising an active ingredient consisting of levobupivacaine (l) and dextrobupivacaine (d) having 75% by mass of levobupivacaine and 25% by mass of dextrobupivacaine or pharmaceutically acceptable salts thereof.

* * * * *